United States Patent
Fernandez Pena et al.

(10) Patent No.: US 10,478,399 B2
(45) Date of Patent: Nov. 19, 2019

(54) MODIFIED RELEASE TABLET COMPOSITION COMPRISING MIRABEGRON

(71) Applicant: SYNTHON B.V., Nijmegen (NL)

(72) Inventors: Agnes Fernandez Pena, Sant Boi de Llobregat (ES); Onne Peter Hilbert Backers, Nijmegen (NL); Jose Velada Calzada, Nijmegen (NL)

(73) Assignee: Synthon B.V., Nijmegen (NL)

( * ) Notice: Subject to any disclaimer, the term of this patent is extended or adjusted under 35 U.S.C. 154(b) by 0 days.

(21) Appl. No.: 15/730,988

(22) Filed: Oct. 12, 2017

(65) Prior Publication Data

US 2019/0110995 A1    Apr. 18, 2019

(51) Int. Cl.
   *A61K 9/20*       (2006.01)
   *A61K 31/4725*    (2006.01)
   *A61K 31/426*     (2006.01)

(52) U.S. Cl.
   CPC .......... *A61K 9/2031* (2013.01); *A61K 9/2054* (2013.01); *A61K 9/2086* (2013.01); *A61K 9/2095* (2013.01); *A61K 31/426* (2013.01); *A61K 31/4725* (2013.01)

(58) Field of Classification Search
   CPC .............. A61K 31/426; A61K 31/4725; A61K 9/2031; A61K 9/2054; A61K 9/2086; A61K 9/2095
   See application file for complete search history.

(56) References Cited

U.S. PATENT DOCUMENTS

| | | | |
|---|---|---|---|
| 6,346,532 B1 | 2/2002 | Maruyama et al. | |
| 8,772,315 B2 | 7/2014 | Suzuki et al. | |
| 2005/0261328 A1 | 11/2005 | Wienrich et al. | |
| 2005/0261369 A1 | 11/2005 | Mehlburger et al. | |
| 2007/0276047 A1 | 11/2007 | Oberegger | |
| 2010/0137358 A1 | 6/2010 | Kharwade et al. | |
| 2010/0144807 A1* | 6/2010 | Takaishi | A61K 9/2031 514/370 |
| 2015/0224087 A1 | 8/2015 | Peddy | |
| 2015/0306090 A1* | 10/2015 | Tsutsui | A61K 31/426 424/464 |
| 2018/0016246 A1* | 1/2018 | Singh | C07D 277/40 |

FOREIGN PATENT DOCUMENTS

| | | |
|---|---|---|
| CN | 104352475 | 2/2015 |
| EP | 2832730 | 2/2015 |
| EP | 2891493 | 7/2015 |
| WO | WO94/06414 A1 | 3/1994 |
| WO | WO99/20607 | 4/1999 |
| WO | WO03/039531 A1 | 5/2003 |
| WO | WO 2004/047838 | 6/2004 |
| WO | WO 2009/057685 | 5/2009 |
| WO | WO2010/038690 | 3/2012 |
| WO | WO 2014/034860 | 3/2014 |
| WO | WO 2015/120110 | 8/2015 |
| WO | WO 2015/129893 | 9/2015 |
| WO | WO 2017/186593 | 11/2017 |
| WO | WO 2017/186598 | 11/2017 |

* cited by examiner

*Primary Examiner* — Michael B. Pallay
(74) *Attorney, Agent, or Firm* — Buscher Patent PLLC

(57) ABSTRACT

The present invention relates to a pharmaceutical composition, particularly a modified release tablet composition comprising mirabegron or a pharmaceutically acceptable salt thereof and to a process for preparing such a composition.

19 Claims, 2 Drawing Sheets

MODIFIED RELEASE TABLET COMPOSITION COMPRISING MIRABEGRON

BACKGROUND OF THE PRESENT INVENTION

The present invention relates to a pharmaceutical composition, particularly a modified release tablet composition comprising mirabegron or a pharmaceutically acceptable salt thereof and to a process for preparing such a composition.

Mirabegron and the pharmaceutically acceptable salts thereof were first disclosed in (International Publication No.) WO 99/20607 (Example 41).

A mirabegron containing pharmaceutical product is approved in many countries all over the world under the brand name Betmiga® in the EU, Myrbetriq® in the US US and Betanis® in Japan as modified release tablets comprising 25 and 50 mg of mirabegron.

Mirabegron is the generic name of (R)-2-(2-aminothiazol-4-yl)-4'-[2-[(2-hydroxy-2-phenylethyl)amino]ethyl]acetic acid anilide,

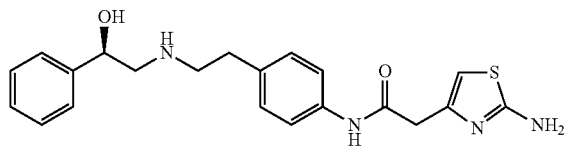 [SMILES: Nc1nc(CC(=O)Nc2ccc(CCNC[C@H](O)c3ccccc3)cc2)cs1]

known as a selective β3 adrenoreceptor agonist and used as a therapeutic agent for overactive bladder, such as overactive bladder accompanied by prostatic hyperplasia, or overactive bladder accompanied by urinary urgency, urinary incontinence, and urinary frequency.

Mirabegron is considered to be a Class III compound according to the Biopharmaceutical Classification System (BCS). That means that it has high solubility and low permeability. Based on the assessment report of Betmiga® published by the European Medicines Agency, mirabegron is soluble in water between neutral to acidic pH.

It is known that the bioavailability of mirabegron is affected by the presence of food in the GI tract. To prevent this food effect, the commercially available pharmaceutical formulation of mirabegron is in the form of a modified-release (MR) tablet formulation based on an orally controlled absorption system (OCAS®) tablet formulation.

The OCAS® is described in WO9406414 (A1). WO9406414 (A1) describes a hydrogel-type sustained-release preparation comprising (1) at least one drug (tamsulosine as one of the examples), (2) an additive which insures penetration of water into the core of the preparation and (3) a hydrogel-forming polymer, wherein said preparation is capable of undergoing substantially complete gelation during its stay in the upper digestive tract including stomach and small intestine and is capable of releasing the drug in the lower digestive tract including colon.

Further, the concept of using a sustained release pharmaceutical composition for reducing or avoiding the changes in pharmacokinetics such as AUC or Cmax accompanied by food intake is known. It was first disclosed in WO03039531 (A1) and was applied to tamsulosin.

The application of the OCAS® system to mirabegron is described in WO2010038690 (A1). It specifically describes a tablet formulation comprising mirabegron or a pharmaceutically acceptable salt thereof, an additive which ensures penetration of water into the pharmaceutical composition, and a polymer which forms a hydrogel.

Due to the use of said additive the preparation undergoes a substantially complete gelation in the upper part of the GI tract, namely stomach and small intestine. The formed gel matrix is then maintained in the hydrated state during the passage through the GI tract for 4 hours or more maintaining a constant release and thus reducing the effects by food, because the drug release from the formulation becomes the rate-limiting step for absorption. This results in a uniform, sustained release of the drug throughout the entire GI tract independently of the presence of food. The 4 hours release period has been selected to simply avoid the effect of food since on the basis of the elimination half-life (T1/2) of mirabegron, which is known to be approximately 18 to 24 hours, a sustained release per se is not needed.

However, we have discovered in our laboratories that not all the formulations encompassed in WO2010038690 (A1) provide the desired release profile for mirabegron and/or show sufficient stability.

There is still a need for a stable pharmaceutical composition of mirabegron or a pharmaceutically acceptable salt thereof having a drug release profile bioequivalent to the commercially available product Betmiga®, Myrbetriq® or Betanis® and that is obtainable by a straight forward and economical process.

BRIEF DESCRIPTION OF THE PRESENT INVENTION

The present invention relates to a modified release tablet composition comprising:
1. 5 to 25 wt % with respect to the total weight of the uncoated tablet of a therapeutically effective dose of mirabegron or a pharmaceutically acceptable salt thereof;
2. polyethylene oxide (PEO) having an average molecular weight of approximately 7,000,000 or a viscosity of 7500 to 10000 cps at a 1% aqueous solution at 25° C. and polyethylene glycol (PEG) having an average molecular weight of approximately 6000 to 10000, preferably 8000, wherein the weight ratio PEO to PEG ranges from 1:3 to 1:4.5.

The present invention also relates to a dry granulation process to prepare such a modified release composition and to a multilayer tablet comprising such a modified release tablet composition.

DETAILED DESCRIPTION OF THE PRESENT INVENTION

Figure 1:
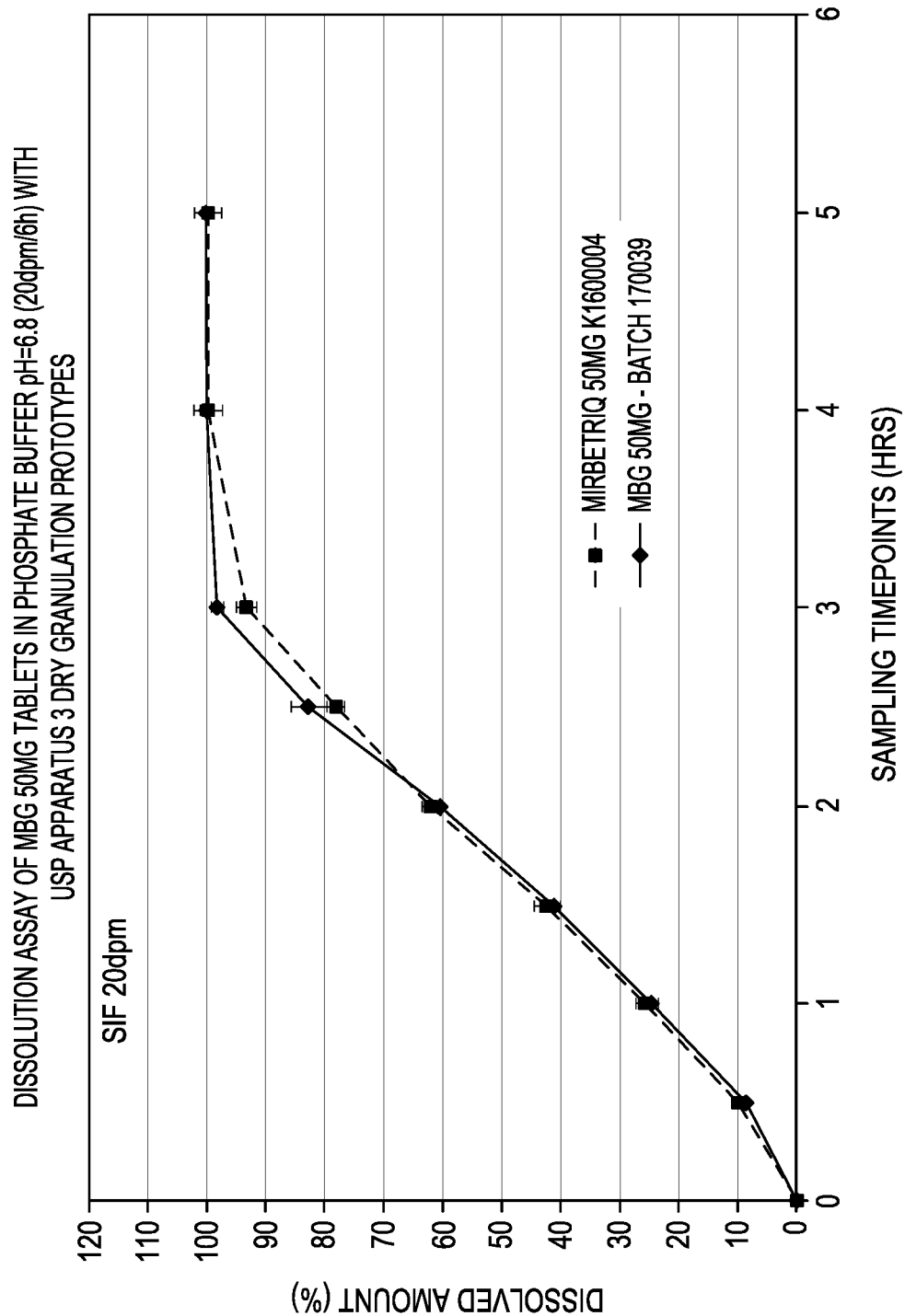
FIG. 1 shows the in vitro dissolution profile of tablet composition in accordance with the present invention (solid line) compared to commercially available tablets (dashed line).

The present invention relates to a modified release tablet composition comprising:

1. 5 to 25 wt % with respect to the total weight of the uncoated tablet of a therapeutically effective dose of mirabegron or a pharmaceutically acceptable salt thereof;
2. polyethylene oxide (PEO) having an average molecular weight of approximately 7,000,000 or a viscosity of 7500 to 10000 cps at a 1% aqueous solution at 25° C. and polyethylene glycol (PEG) having an average molecular weight of approximately 6000 to 10000, preferably 8000, wherein the weight ratio PEO to PEG ranges from 1:3 to 1:4.5.

The modified release tablet compositions of the present invention are stable and show an in vitro dissolution profile wherein mirabegron is released 15-35% within 1 hour, at least 50% within 2 hours and at least 90% within 3 hours when the composition is subjected to a dissolution study in 250 ml phosphate buffer (pH 6.8) using a USP apparatus 3 at 20 rpm at 37° C.

The term "stable" as used herein means that tablets comply with the dissolution specification when subjected to a 6 months stability study at the accelerated stability conditions of 40° C. and 75% RH.

The term "total weight" refers to the total weight of the uncoated tablet.

Modified release hydrogel tablets based on polyethylene oxide tend to suffer changes in their dissolution release profile when exposed to oxygen or UV light not complying with the dissolution specifications during the stability study. This is relevant since it may cause loss of the desired therapeutic control of the modified release tablets. Particularly the weight ratio of polyethylene oxide in the tablet and the average molecular weight of the polyethylene oxide may affect the stability of the tablets and their dissolution profile when exposed to a 6 months stability study at the accelerated stability conditions of 40° C. and 75% RH.

Preferably the pharmaceutical tablet composition of the present invention is stabilized by an oxygen and UV light barrier like for example a primary packaging material like Aluminium/Aluminium blister foil or a light resistant HDPE container.

The modified release tablet composition of the present invention is described in further detail hereinafter.

A therapeutically effective dose of mirabegron or a pharmaceutically acceptable salt thereof is present at a weight ratio of 5 to 25% in the tablet with respect to the total weight of the uncoated tablet. In a particular embodiment mirabegron or a pharmaceutically acceptable salt thereof has a particle size distribution of D90 between 5 and 150 μm. Preferably the D90 is between 10 and 60 μm.

The modified release tablet composition of the present invention further comprises PEO having an average molecular weight of approximately 7,000,000 or a viscosity of 7500 to 10000 cps at a 1% aqueous solution at 25° C. and PEG having an average molecular weight of approximately 6000 to 10000, preferably 8000.

Polyethylene oxide is a nonionic homopolymer of ethylene oxide, represented by the formula [(OCH$_2$CH$_2$)n], in which n represents the average number of oxyethylene groups and varies from about 2,000 to 160,000; the molecular weights range from about 100,000 to 7 million. Polyethylene oxide occurs as a white to off-white, free-flowing powder. It is available in different grades that vary in viscosity profiles in aqueous isopropyl alcohol solutions. Polyethylene oxide may degrade by oxidation and commercially available polyethylene oxide may therefore contain a suitable antioxidant.

Polyethylene oxide is a very hydrophilic polymer. Upon contact with an aqueous medium, it hydrates rapidly to form a gel layer to support the release of the active. Typically the drug release occurs by combination of two mechanisms; diffusion and erosion. For a water soluble drug substance as mirabegron, diffusion of the active through the gel layer is the dominant mechanism but gradual erosion of the gel, exposing fresh surfaces containing drug to the dissolution media, may also take place.

Different ratios of polyethylene oxide 7,000,000 (e.g. Polyethylene oxide 20 NF or Polyox WSR 303 NF) and PEG having an average molecular weight of approximately 6000 to 10000 were evaluated in order to study its influence on drug dissolution. The inventors have surprisingly found that when the weight ratio PEO to PEG ranges from 1:3 to 1:4.5, preferably from 1:3 to 1:4, more preferably from 1:3.2 to 1:3.8 the mirabegron formulation is bioequivalent to the commercial Betmiga®, Myrbetriq® or Betanis®. This specific weight ratio has shown good results in the achievement of the desired dissolution profile and compliance to the dissolution specification during the stability testing.

FIG. 1 shows the dissolution profile of a formulation with a weight ratio PEO having an average molecular weight of approximately 7,000,000 and PEG having an average molecular weight of approximately 8000, with respect to the total weight of the uncoated tablet in comparison to the reference product Mirbetriq®.

The qualitative and quantitative compositions of the tested tablet are disclosed in Table 1.

Polyethylene oxide having an average molecular weight of 7,000,000 forms a high viscosity matrix typically leading to a decrease in the diffusion of the drug, slowing excessively the dissolution rate. However, we have found that PEO with an average molecular weight of 7,000,000 can be used minimising this behaviour by using it in combination with PEG having an average molecular weight of approximately 6000 to 10000 in the specific weight ratio of the invention. When the weight ratio PEO to PEG ranges from 1:3 to 1:4.5, preferably from 1:3 to 1:4, more preferably from 1:3.2 to 1:3.8, it decreases the gel viscosity on the surface of the tablet which accelerates the diffusion of the drug from the gel layer. Additionally, using the weight ratio of the invention results in less stability problems, when compared with the examples provided in WO2010038690 (A1).

The PEO 7M has a tendency to oxidise. When the PEO oxidises, it becomes less viscous, accelerating the dissolution. Optionally to further diminish the oxidation, the modified release tablet of the present invention can additionally comprise an antioxidant. A preferred antioxidant is butylated hydroxytoluene (BHT).

Additionally the present invention may comprise other pharmaceutically acceptable excipients, for example, binders, diluents, lubricants, and glidants.

Binders which are suitable for use in accordance with the present invention include hydroxypropyl cellulose, povidone, dihydroxy propylcellulose, and sodium carboxyl methylcellulose. Binders are preferably used in an amount of from 1 to 5 wt % with respect to the total weight of the uncoated tablet. A preferred binder is hydroxypropylcellulose.

Diluents are fillers which are used to increase the bulk volume of a tablet or capsule. Generally, by combining a diluent with the active pharmaceutical ingredient, the final product is given adequate weight and size to assist in production and handling. Diluents give volume to low active dose tablets. The present invention may comprise one or more diluents. Suitable examples of diluents to be used in accordance with the present invention include starch, pregelatinized starch, microcrystalline cellulose (MCC), calcium phosphate, lactose, sorbitol, mannitol. In a preferred embodiment one of the diluents is MCC. In a more preferred embodiment the amount of MCC is 5 to 25% with respect to the total weight of the uncoated tablet. Most preferably, the amount of MCC is 8 to 20% with respect to the total weight of the uncoated tablet.

The tablet composition of the invention may also contain a lubricant. Lubricants are generally used in order to reduce sliding friction. In particular, to decrease friction at the interface between a tablet's surface and the die wall during ejection, and reduce wear on punches and dies. Suitable lubricants to be used in accordance with the present invention include magnesium stearate, calcium stearate, stearic acid, glyceryl behenate, hydrogenated vegetable oil, and glycerine fumarate. The tablet composition of the invention may also contain a glidant. Glidants enhance product flow by reducing interparticulate friction. A suitable example is colloidal silicon dioxide.

Lubricants and glidants preferably are used in a total amount of from 0.05 to 5 wt % with respect to the total weight of the uncoated tablet.

In a preferred embodiment, the tablet composition of the present invention comprises the following ingredients, based on the total weight of the composition:
1. 5 to 25 wt % with respect to the total weight of the uncoated tablet of a therapeutically effective dose of mirabegron or a pharmaceutically acceptable salt thereof;
2. polyethylene oxide (PEO) having an average molecular weight of approximately 7,000,000 or a viscosity of 7500 to 10000 cps at a 1% aqueous solution at 25° C. and polyethylene glycol (PEG) having an average molecular weight of approximately 6000 to 10000, preferably 8000, wherein the weight ratio PEO to PEG ranges from 1:3 to 1:4.5;
3. A binder in an amount of from 1% to 5 wt % with respect to the total weight of the uncoated tablet;
4. A lubricant in an amount from 0.05% to 5 wt % with respect to the total weight of the uncoated tablet; and
5. Optionally, MCC, preferably in an amount 5 to 25% with respect to the total weight of the uncoated tablet.

In one embodiment of the present invention, the therapeutically effective dose of mirabegron is 25 mg or 50 mg.

The pharmaceutical composition of the present invention can be used in combination with another API to form a multilayer tablet. A preferred API to be used in combination with mirabegron is solifenacin or an acceptable salt thereof.

The present invention further relates to a tablet composition as described hereinabove, prepared by a dry-granulation process by slugging or roller compaction.

Said process comprises the steps of:
1. Mixing mirabegron, polyethylene oxide, polyethylene glycol and one or more further pharmaceutically acceptable excipients to form a mixture;
2. Compacting the resulting mixture;
3. Further mixing the obtained granulate with one or more further pharmaceutically acceptable excipients to form a further mixture;
4. Compressing the mixture obtained in step (3) into a tablet;
5. Optionally, coating the tablet.

The granules of the present invention typically have a particle size distribution $D_{90}$ equal or less than 1 mm. The pharmaceutical compositions described herein can be made using conventional methods and equipment well-known in the art.

The modified release tablet compositions of the present invention are stable and show an in vitro dissolution profile wherein mirabegron is released 15-35% within 1 hour, at least 50% within 2 hours and at least 90% within 3 hours when the composition is subjected to a dissolution study in 250 ml phosphate buffer (pH 6.8) using a USP apparatus 3 at 20 rpm at 37° C.

The present invention is illustrated by the following Examples.

EXAMPLES

TABLE 1

Qualitative and quantitative formula example1

| | Components | mg/tablet | % |
|---|---|---|---|
| Intra-granular | Mirabegron | 50.00 | 20.00 |
| | PEO 7,000,000 (PEO-20NF) | 41.25 | 16.50 |
| | Polyethylene glycol 8,000 P | 148.35 | 59.34 |
| | Hydroxypropyl cellulose (Klucel EXF) | 7.50 | 3.00 |
| | BHT | 0.40 | 0.16 |
| | Magnesium stearate | 1.25 | 0.50 |
| Extra-granular | Magnesium stearate | 1.25 | 0.50 |
| Core weight | | 250.00 | 100.0 |
| Opadry Yellow 03F220071 | | 7.50 | — |
| Final weight | | 257.50 | |

Weight ratio PEO 7,000,000 to Polyethylene glycol 8,000 P 1:3.60

TABLE 2

Qualitative and quantitative formula comparative example 2

| | Components | mg/tablet | % |
|---|---|---|---|
| Intra-granular | Mirabegron | 50.00 | 20.00 |
| | PEO 7,000,000 (PEO-20NF) | 31.30 | 12.64 |
| | Polyethylene glycol 8,000 P | 158.40 | 63.36 |
| | Hydroxypropyl cellulose (Klucel EXF) | 7.50 | 3.00 |
| | BHT | 0.40 | 0.16 |
| | Magnesium stearate | 1.25 | 0.50 |
| Extra-granular | Magnesium stearate | 1.25 | 0.50 |
| Core weight | | 250.00 | 100.0 |
| Opadry Yellow 03F220071 | | 7.50 | — |
| Final weight | | 257.50 | |

Weight ratio PEO 7,000,000 to Polyethylene glycol 8,000 P 1:5.01

TABLE 3

Qualitative and quantitative formula comparative example 3

| | Components | mg/tablet | % |
|---|---|---|---|
| Intra-granular | Mirabegron | 50.00 | 20.00 |
| | PEO 7,000,000 (PEO-20NF) | 60.00 | 24 |
| | Polyethylene glycol 8,000 P | 129.60 | 51.84 |
| | Hydroxypropyl cellulose (Klucel EXF) | 7.50 | 3.00 |
| | BHT | 0.40 | 0.16 |
| | Magnesium stearate | 1.25 | 0.50 |

TABLE 3-continued

Qualitative and quantitative formula comparative example 3

| | Components | mg/tablet | % |
|---|---|---|---|
| Extra-granular | Magnesium stearate | 1.25 | 0.50 |
| | Core weight | 250.00 | 100.0 |
| | Opadry Yellow 03F220071 | 7.50 | — |
| | Final weight | 257.50 | |

Weight ratio PEO 7,000,000 to Polyethylene glycol 8,000 P 1:2.16

Figure 2:
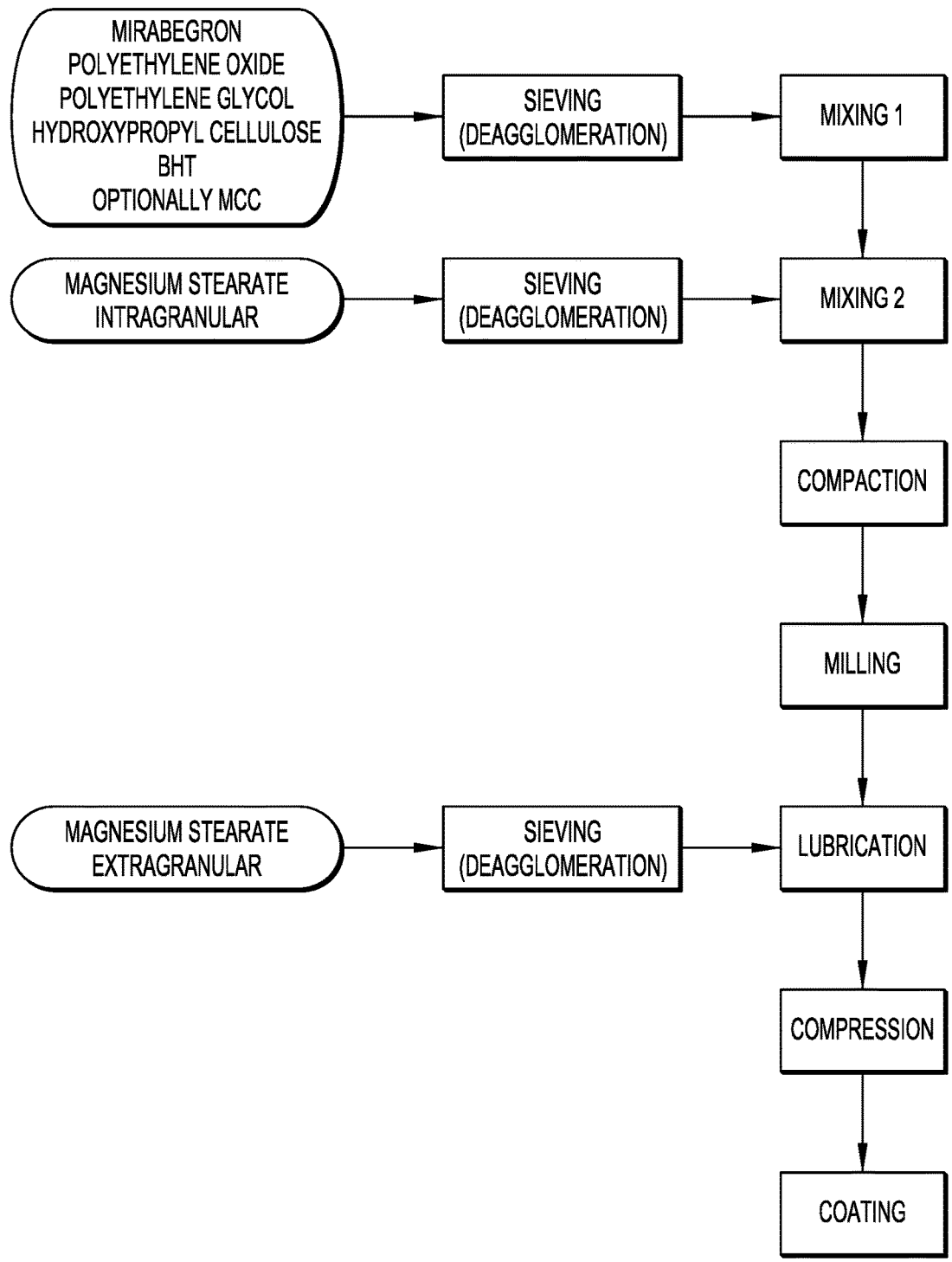
FIG. 2 depicts the process used to make the tablets of example 1, comparative example 2 and comparative example 3.

The tablets of example 1, comparative example 2 and comparative example 3 were made according to the process depicted in FIG. 2:

In Vivo Bioequivalence Study

In a single dose bioavailability study of mirabegron, modified release tablets produced according to example 1 and comparative example 2 and 3 were compared with that of Myrbetriq®/Betmiga® 50 mg in healthy adult volunteers subjects under fasting conditions.

TABLE 1

Comparative pharmacokinetic parameters of present invention vs commercial Myrbetriq ® Betmiga ® 50 mg

| Examples | Ratio PEG/PEO | T/R Cmax(%) | T/R AUCt(%) |
|---|---|---|---|
| 1 | 3.60 | 100.19 | 97.3 |
| Comparative 2 | 5.01 | 173.45 | 129.63 |
| Comparative 3 | 2.16 | 56.01 | 63.03 |

FIG. 1 shows the in vitro dissolution profiles of 50 mg mirabegron modified release tablets prepared following example 1 in accordance with the present invention (shown as solid line) as compared to commercially available Myrbetriq® 50 mg tablets (shown as dashed line). The dissolution was performed in phosphate buffer having a pH of 6.8 using USP Apparatus 3 (20 dpm).

The invention claimed is:

1. A modified release tablet composition comprising:
   a) 5 to 25 wt % with respect to the total weight of the uncoated tablet of a therapeutically effective dose of mirabegron or a pharmaceutically acceptable salt thereof; and
   b) polyethylene oxide (PEO) having an average molecular weight of approximately 7,000,000 or a viscosity of 7500 to 10000 cps at a 1% aqueous solution at 25° C. and polyethylene glycol (PEG) having an average molecular weight of approximately 6000 to 10000, wherein the weight ratio PEO to PEG ranges from 1:3 to 1:4.5;
   wherein said tablet exhibits an in vitro dissolution profile that meets the following release criteria: 15%-35% of mirabegron is released within 1 hour, at least 50% of mirabegron is released within 2 hours, and at least 90% of mirabegron is released within 3 hours, wherein said dissolution profile is measured in 250 ml phosphate buffer (pH 6.8) using USP apparatus 3 at 20 dpm and 37° C.

2. The modified release tablet composition according to claim 1, wherein the weight ratio PEO to PEG ranges from 1:3 to 1:4.

3. The modified release tablet composition according to claim 1, further comprising microcrystalline cellulose (MCC).

4. The modified release tablet composition according to claim 1, wherein mirabegron has a particle size distribution of D90 between 10 and 60 µm.

5. The modified release tablet composition according to claim 1, wherein said polyethylene glycol (PEG) has an average molecular weight of approximately 8000.

6. The modified release tablet composition according to claim 1, wherein said tablet is stable such that a dissolution profile obtained after storing a tablet for 6 months at 40° C. and 75% RH meets said release criteria.

7. The modified release tablet composition according to claim 1, wherein the weight ratio PEO to PEG ranges from 1:3.2 to 1:3.8 and said polyethylene glycol (PEG) has an average molecular weight of approximately 8000.

8. The modified release tablet composition according to claim 1, wherein said tablet contains 25 mg or 50 mg of mirabegron.

9. A multilayer tablet comprising the modified release tablet composition according to claim 1.

10. The multilayer tablet according to claim 9, which is a bilayer tablet.

11. The multilayer tablet according to claim 9, further comprising solifenacin.

12. A modified release tablet composition comprising the following ingredients:
   a) a therapeutically effective dose of mirabegron or a pharmaceutically acceptable salt thereof in an amount of from 5 to 25 wt % with respect to the total weight of the uncoated tablet;
   b) polyethylene oxide (PEO) having an average molecular weight of approximately 7,000,000 or a viscosity of 7500 to 10000 cps at a 1% aqueous solution at 25° C. and polyethylene glycol (PEG) having an average molecular weight of approximately 6000 to 10000, wherein the weight ratio PEO to PEG ranges from 1:3 to 1:4.5;
   c) a binder in an amount of from 1 to 5 wt % with respect to the total weight of the uncoated tablet;
   d) a lubricant in an amount from 0.05% to 5 wt % with respect to the total weight of the uncoated tablet; and
   e) optionally microcrystalline cellulose (MCC);
   wherein said tablet exhibits an in vitro dissolution profile that meets the following release criteria: 15%-35% of mirabegron is released within 1 hour, at least 50% of mirabegron is released within 2 hours, and at least 90% of mirabegron is released within 3 hours, wherein said dissolution profile is measured in 250 ml phosphate buffer (pH 6.8) using USP apparatus 3 at 20 dpm and 37° C.

13. The modified release tablet composition according to claim 12, prepared by a dry-granulation process, which process comprises:
   a) mixing mirabegron, polyethylene oxide, polyethylene glycol and one or more further pharmaceutically acceptable excipients to form a mixture;
   b) compacting the resulting mixture to form a granulate;
   c) further mixing the obtained granulate with one or more further pharmaceutically acceptable excipients to form a further mixture;
   d) compressing the mixture obtained in step (c) into a tablet; and
   e) optionally, coating the tablet.

14. The modified release tablet composition according to claim 13, wherein the compacting step (b) is performed by slugging or by a roller compactor.

15. The modified release tablet composition according to claim 13, wherein the granules have a particle size distribution $D_{90}$ equal or less than 1 mm.

16. The modified release tablet composition according to claim 12, wherein said polyethylene glycol (PEG) has an average molecular weight of approximately 8000.

17. The modified release tablet composition according to claim 12, wherein said binder is hydroxypropylcellulose.

18. The modified release tablet composition according to claim 12, wherein the weight ratio PEO to PEG ranges from 1:3 to 1:4.

19. The modified release tablet composition according to claim 12, wherein mirabegron has a particle size distribution of D90 between 10 and 60 μm.

* * * * *